United States Patent
Plewes et al.

(10) Patent No.: US 6,459,923 B1
(45) Date of Patent: Oct. 1, 2002

(54) INTERVENTION BED FOR A MEDICAL IMAGING DEVICE

(75) Inventors: Donald Bruce Plewes, Toronto (CA); Gregory A. Repinski, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 19 days.

(21) Appl. No.: 09/718,777

(22) Filed: Nov. 22, 2000

(51) Int. Cl.$^7$ .............................................. A61B 5/00
(52) U.S. Cl. .................. 600/411; 600/415; 600/425; 600/427; 5/601; 5/611; 378/209
(58) Field of Search ................................. 600/411, 415, 600/427, 425, 407; 5/601, 611, 612; 378/208, 209

(56) References Cited

U.S. PATENT DOCUMENTS

| | | | |
|---|---|---|---|
| 4,567,894 A | * 2/1986 | Bergman | 600/415 |
| 4,582,310 A | * 4/1986 | Hahn | 5/611 |
| 4,613,121 A | * 9/1986 | Hahn | 5/601 |
| 4,771,785 A | * 9/1988 | Duer | 600/415 |
| 5,542,906 A | * 8/1996 | Herrmann et al. | 600/427 |
| 5,590,429 A | 1/1997 | Boomgaarden et al. | 5/600 |
| 5,590,653 A | * 1/1997 | Aida et al. | 600/411 |
| 5,596,779 A | 1/1997 | Meek | 5/600 |
| 5,600,858 A | 2/1997 | Baer | 5/601 |
| 5,729,849 A | 3/1998 | Garakani | 5/618 |
| 5,808,468 A | 9/1998 | Bis et al. | 324/318 |

* cited by examiner

Primary Examiner—Ruth S. Smith
(74) Attorney, Agent, or Firm—Foley & Lardner; Peter J. Vogel; Michael A. Della Penna

(57) ABSTRACT

A modular intervention bed for use with a medical tomographic imaging system having an associated patient transport device and an imaging device. The modular intervention bed comprises a trestle configured to engage a patient transport device, with the trestle having an intervention area. A patient couch movably mounted on the trestle, with the patient couch defining an opening corresponding to the intervention area. The couch comprises a plurality of patient mats with each mat connected to at least one other mat, a pair of rollers mounted on each mat in a spaced apart relationship with each roller proximate an outside edge of each mat. The modular intervention bed can be reconfigured by adding or removing a mat thereby moving the intervention area and opening to correspond with the portion of a patient under investigation during an intervention procedure guided by a medical tomographic imaging system.

22 Claims, 4 Drawing Sheets

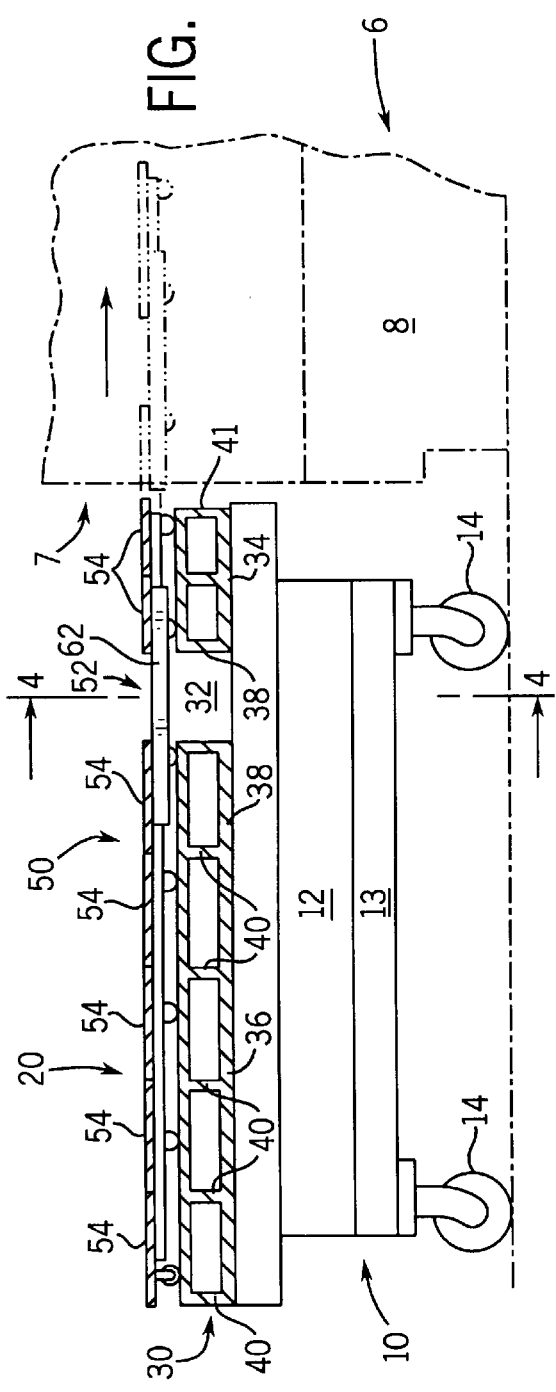

INTERVENTION BED FOR A MEDICAL IMAGING DEVICE

FIELD OF THE INVENTION

The invention relates to a patient bed, and more particularly to a modular intervention patient bed for use with a medical tomographic imaging system.

BACKGROUND OF THE INVENTION

The use of medical tomographic imaging systems like magnetic resonance imaging (MRI) and computed tomography imaging (CT) is well known in the medical field. During the medical imaging procedure, it is necessary for the patient to maintain the position initially established by the operator of the system in order to obtain clear and proper images in the particular medical tomographic imaging system being utilized. In some instances, this even requires the patient to hold its breath during the image acquisition time period. Some procedures that are undertaken during an imaging session includes the intervention of the patient by a probe for purposes of obtaining a biopsy sample or for a therapeutic procedure. The medical imaging system is utilized to guide the operator in moving the probe to the selected portion of the patient's body under study. One example of such procedure includes the use of an MRI system to guide during a breast biopsy and conduct various forms of image guided thermal ablation.

A typical MRI system offers many technical advantages including excellent image quality, high resolution, near real-time capability and good position for magnetic resonant thermometry. However, the confining geometry of the MRI system poses a severe limit on patient access. Under such conditions, image data is gathered under an appropriate imaging regime, (i.e., contrast enhancement) and then some form of intervention is carried out with the patient positioned in the fringe field at the entry of the MR magnet bore. As mentioned above, this approach requires that the patient configuration not change between the image procedure and the intervention procedure. In the case of a breast intervention, the patient is prone on the bed with her breast pendent into some form of coil arrangement that serves to immobilize the breast and provides a framework for intervention. However, the space for mounting intervention devices below the patient on the current type of patient bed is very limited. A typical patient bed has a curvature that further limits lateral access to a patient's breast during the imaging procedure of such patient.

Thus, there is the need for a patient bed that facilitates intervention procedures during a medical tomographic imaging session. There is a further need for a patient bed for use with a medical tomographic imaging system that provides access for placement of specialized interventional devices. There is an additional need for a patient bed for use with a medical tomographic imaging system that can be used with an existing patient transportation device.

SUMMARY OF THE INVENTION

One embodiment of the present invention, provides a modular intervention bed for use with a medical tomographic imaging system having an associated patient transport device and an imaging device. The modular intervention bed comprises a trestle configured to engage the patient transport device, with the trestle having an intervention area. A patient couch movably mounted on the trestle, with the patient couch defining an opening corresponding to the intervention area. The couch comprises a plurality of patient mats with each mat connected to at least one other mat, a pair of rollers mounted on each mat in a spaced apart relationship with each roller proximate an outside edge of each mat. A guide is mounted on the trestle with the guide mounted and aligned with the rollers on each mat. A linking beam with each end of the beam attached to a mat maintains each such mat in a spaced apart relationship and defines the opening corresponding to the intervention area of the trestle.

Another embodiment of the modular intervention bed provides the trestle with a first portion and a second portion, with each portion engaging the patient transport device with the first portion a selected distance from the second portion, wherein the distance between the two portions defines the intervention area of the trestle. The modular intervention bed can be reconfigured by adding or removing a mat thereby moving the intervention area and opening to correspond with the portion of a patient under investigation during an intervention procedure guided by a medical tomographic imaging system.

Another embodiment of the modular intervention bed for use with a medical tomographic imaging system having an associated patient transport device and an imaging device includes a means for supporting configured to engage the patient transport device with the means for supporting having an intervention area and a means for reclining movably mounted on the means for supporting, with the patient means for reclining defining an opening corresponding to the intervention area.

According to another aspect of the present invention, there is a method for providing access to a patient on a patient transport device for a medical imaging procedure comprising the steps of placing a trestle on the patient transport device with the trestle having an intervention area. Placing a movable patient couch on the trestle, with the patient couch having an opening corresponding to the intervention area, and securing the trestle to the patient transport device. Placing a patient on the patient couch and orientating the patient on the couch to expose the patient in the intervention area then performing the medical imaging procedure on the patient including accessing the patient in the intervention area. Another aspect of the present invention includes the steps of reconfiguring the couch by adding or removing a mat, reconfiguring the trestle to correspond to the reconfigured couch and aligning the reconfigured couch with the reconfigured trestle, wherein a new intervention area is provided for access to the patient.

BRIEF DESCRIPTION OF THE DRAWINGS

FIG. 2 is a sectional side view of the modular intervention bed illustrated in FIG. 1 along the lines 2—2.

FIG. 3 is a side view illustration of an examplary embodiment of a modular intervention bed configured with an intervention area in the trestle and corresponding opening in the couch different from the intervention area and opening illustrated in FIGS. 1 and 2.

DETAILED DESCRIPTION OF THE EXEMPLARY EMBODIMENTS

Figure 1:
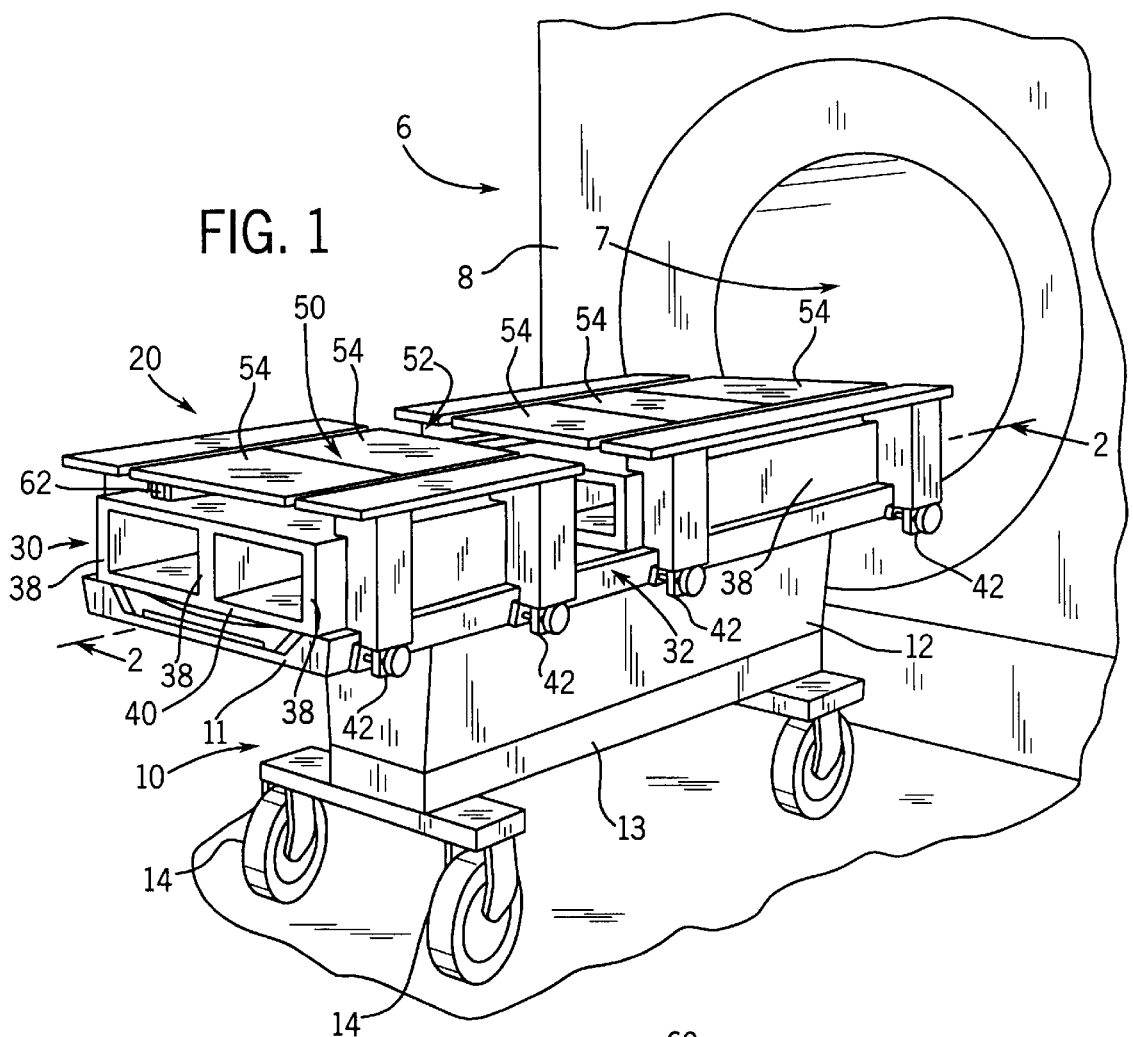
FIG. 1 is a perspective illustration of an examplary embodiment of a modular intervention bed configured to engage a patient transport device adjacent to a medical tomographic imaging device.
Figure 4:
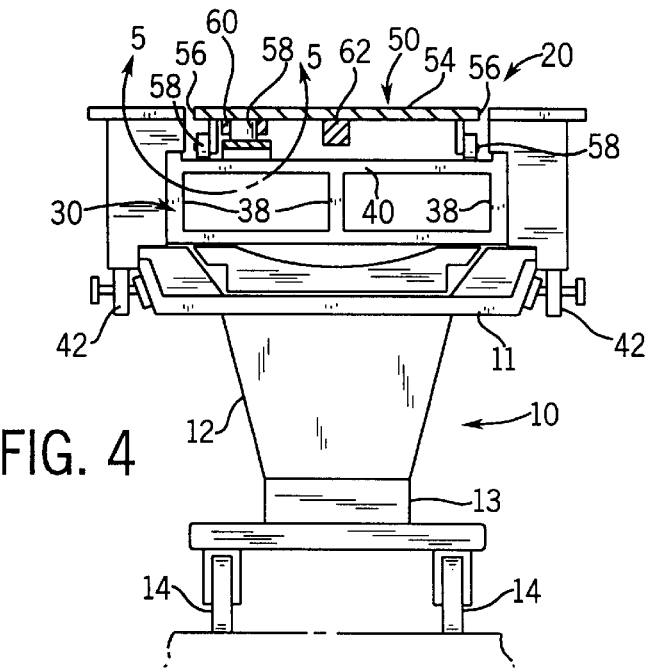
FIG. 4 if an end sectional view of the modular intervention bed illustrated in FIG. 2, along the line 4—4.
Figure 7:
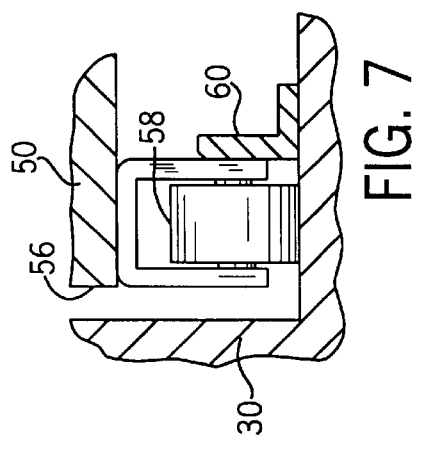
FIG. 7 is a partial end view illustration of a roller coupled to patient mat of a patient couch with the roller in a horizontal aspect with espect to the mat and illustrating an examplary embodiment of a guide.
Figure 6:
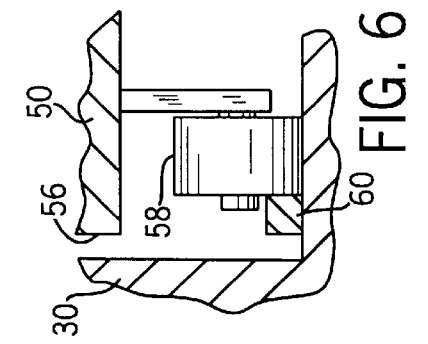
FIG. 6 is a partial end view illustration of a roller coupled to a patient mat of a patient couch with the roller in a vertical aspect with respect to the mat and illustrating an examplary embodiment of a guide.
Figure 5:
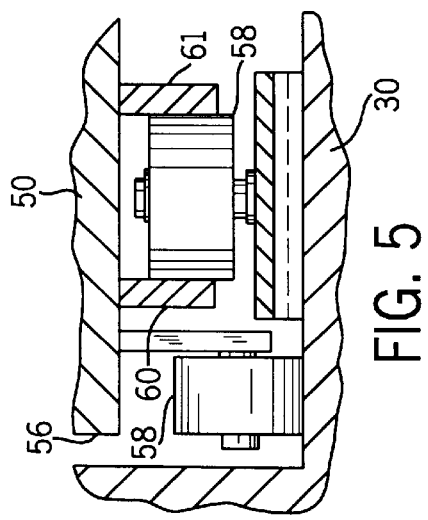
FIG. 5 is a partial sectional view of the modular intervention bed illustrated in FIG. 4, along the line 5—5, showing an examplary embodiment of rollers mounted on a patient mat of the patient couch, with one roller in a vertical aspect and one roller in a horizontal aspect each with respect to the patient mat.
Figure 8:
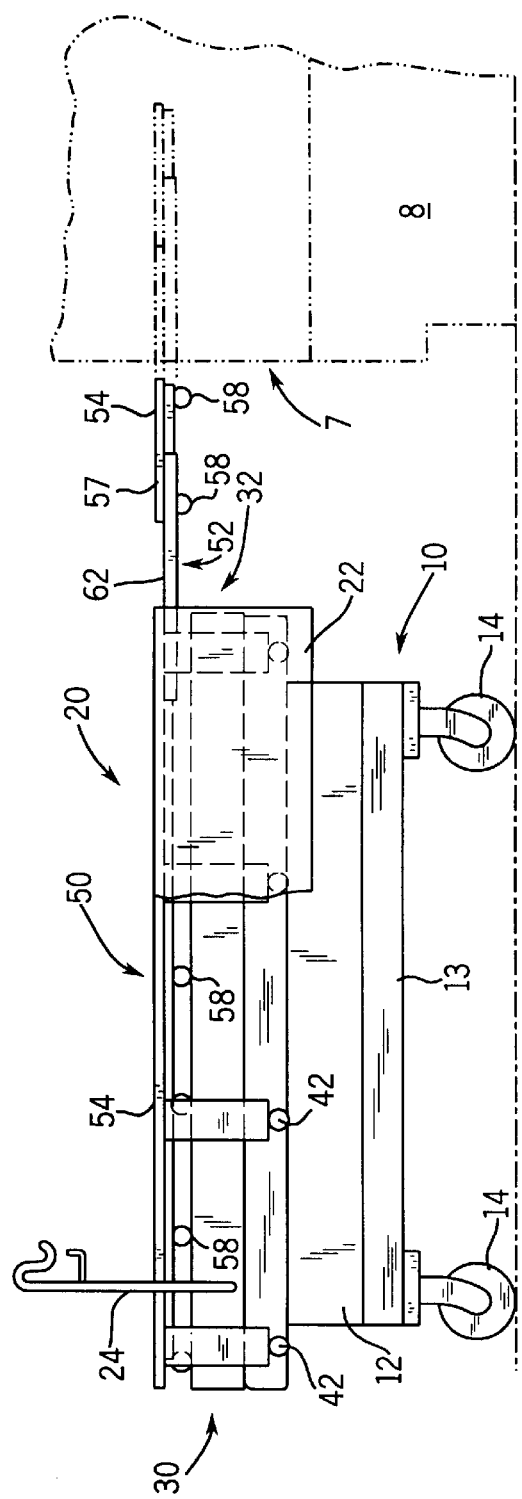
FIG. 8 is a partial side view illustration of an exemplary embodiment of a modular intervention bed illustrating an equipment attachment and a side cover, with a portion of the patient couch over an edge of the trestle in a cantilevered fashion.
Figure 9:
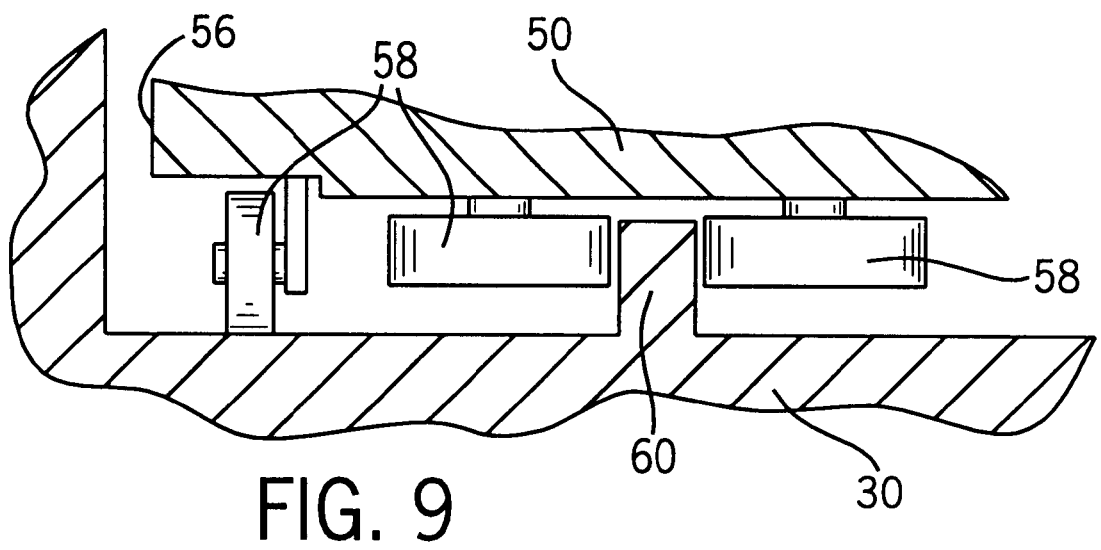
FIG. 9 is a partial sectional view of a modular intervention bed showing an exemplary embodiment of rollers mounted on a patient mat of the patent couch, with one roller in a vertical aspect and a pair of rollers in a horizontal aspect each with respect to the patient mat and with a guide between the two horizontal rollers.

A medical tomographic imaging system 6 such as a magnetic resonant imaging (MRI) or a computed tomography imaging (CT) device have an area, such as a bore 7, in which a patient is placed during the medical imaging procedure. While in the bore 7, the patient is exposed to the electromagnetic energy from the particular imaging device 8, the data from which is used to create an image of the particular organ or area of the patient under study. A patient transport device 10 is associated with the imaging device 8 and is used to bring the patient to and from the medical tomographic imaging system's imaging device 8. The patient transport device 10 generally includes a table top 11, an elevation portion 12, and a base 13 supported by wheels 14. The patient lies on the table top 11 and is moved vertically by the elevation portion 12 of the patient transport device 10 and horizontally by the table top 11.

During the medical imaging procedure, an operator of the medical tomographic imaging system 6 may desire or is required to use a probe on the patient and insert the probe into an area of the patient's body that is under study. The operator will use the imaging device 8 to assist in guiding the probe to the specific location selected by the operator during the procedure. During the medical imaging procedure it is imperative that the patient maintain the position initially established by the operator of the imaging device 8 during the image data acquisition time period and when the probe is inserted into the patient. Because of the confining geometry of the medical imaging system 6, there are severe limits on patient access by the operator of the imaging system. This is particularly true when the patient is placed in the bore 7 of the medical tomographic imaging device 8. A patient bed that provides appropriate access for a specific imaging procedure can be designed, however, it would be limited in use to only those specific types of medical imaging procedures for which it is designed. Such bed would be very expensive and a different bed design would be needed for a different type of medical imaging procedure.

The present modular intervention bed 20 for use with a medical tomography imaging system 6 that has an associated patient transport device 10 and an imaging device 8 comprises a trestle 30 and a patient couch 50. The trestle 30 is configured to engage the patient transport device 10 with the trestle 30 having an intervention area 32. The patient couch 50 is movably mounted on the trestle 30 with the patient couch 50 defining an opening 52 corresponding to the intervention 20 area 32. The trestle is placed on the table top 11 of the patient transport device 10 and clamped in place by clamps 42 configured to engage the table top 11. The table top 11 of the patient transport device 10 is typically locked and movement of the patient in the horizontal direction is accomplished by the patient couch 50 as will be described hereafter.

The patient couch 50 comprises a plurality of patient mats 54 with each mat 54 connected to at least one other mat 54. A roller 58 is mounted on each mat in a spaced apart relationship with each roller 58 proximate an outside edge 56 of each mat 54. A guide 60 is mounted on the trestle 30 with the guide mounted and aligned with the roller 58 on each mat 54. The rollers 58 can be of any convenient or conventional size and can be orientated in a vertical or horizontal aspect with respect to the trestle 30. The rollers 58 can be made out of any non-metallic material such as glass, an engineered plastic or wood, with the preferred embodiment being a delrin/glass composition. A linking beam 62 with each end of the beam 62 attached to a mat 54 maintains each such mat 54 in a spaced apart relationship and defines the opening 52 corresponding to the intervention area 32. The linking beam 62 can be attached at various locations on the mat 54 and is held in place by a clip, a socket or pin or screw or the like which allows a ready reconfiguration of the modular intervention bed to accommodate the patient and the medical imaging procedure to be performed on that patient. A second guide 61 can be mounted on the trestle 30 with each guide 60, 61 mounted and aligned with the rollers 58 along each outside edge 56 of each mat 54. The second guide 61 assists in maintaining lateral position of the mats 58.

The trestle 30 comprises a first portion 34 and a second portion 36 with each portion 34, 36 engaging the patient transport device 10 with the first portion 34 a selected distance from the second portion 36, wherein the distance between the two portions 34, 36 defines the intervention area 32. One embodiment of the modular intervention bed 20 provides the trestle 30 with a pair of risers 38 maintained in a spaced apart relationship with each other by at least one cross piece 40 connected to each riser 38. A preferred exemplary embodiment provides two cross pieces with the two risers 38 forming a box framework to which additional risers 38 and cross pieces 40 can be added or deleted as selected by the operator of the medical tomographic imaging system 6 to reconfigure the modular intervention bed. The patient couch 50 can also be reconfigured by adding or removing a mat 54 so that the couch 50 corresponds with the trestle 30 in the modular intervention bed 20. The opening 52 in the patient couch 50 corresponds to the intervention area 32 of the trestle 30. When the patient is placed on the patient couch 50, the area of the patient, such as a breast for a breast biopsy procedure, extends into or over the opening 52 and the intervention area 32 thereby allowing access for the operator, as well as access for a probe or other instrumentality used in the medical imaging procedure being conducted.

The clamp 42 secures the riser 38 of the modular intervention bed 20 to the patient transport device 10. A preferred exemplary embodiment of a modular intervention bed would provide at least two clamps 42, one on each side of the patient transportation device 10. Another preferred embodiment would provide 4 clamps 42 with two clamps on each side of a patient transportation device 10 securing the risers 38 of the trestle 30 to the table top 11 of the patient transportation device 10. A side cover 22 attached to at least one of the trestle 30 and the couch 50 on each side of the modular intervention bed 20 provides an aesthetic attribute to the modular intervention bed 20 and also prevents the risers 38 from exposure to unnecessary intrusions.

Because the modular intervention bed 20 is used with magnetic resonant imaging systems, a preferred exemplary embodiment of the modular intervention bed provides that the trestle 30, the couch 50, the guides 60, 61 and the rollers 58 are composed of non-metallic material such as glass, wood, an engineered plastic or the like.

The modular intervention bed 20 includes a method for providing access to a patient on a patient transportation device 10 for a medical imaging procedure, the method comprising the steps of placing a trestle 30 on the patient transportation device 10 with the trestle 30 having an intervention area 32. Placing a movable patient couch 50 on the trestle 30 with the patient couch 50 having an opening 52 corresponding to the intervention area 32. Securing the trestle to the patient transportation device with a clamp 42 and placing a patient on the patient couch 50. Orientating the patient on the couch to expose the patient in the intervention area and performing the medical imaging procedure on the patient including accessing the patient in the intervention area. The method of providing access to a patient on a patient transport device for a medical imaging procedure includes the steps of reconfiguring the couch 50 by adding or removing a mat 54, reconfiguring the trestle 30 to correspond to the reconfigured couch and aligning the reconfigured couch 50 with the reconfigured trestle 30 wherein a new intervention area 32 is provided for access to the patient. By constructing the modular intervention bed in a modular fashion, the intervention area 32 can be positioned in different regions of the bed 20 so that different kinds of interventions can be accomplished. For example, the opening 52 in the patient couch 50 and aligned with the intervention area 32 in the trestle 30 can be positioned below the cervical, thoracic, abdominal or lumbar regions of the patient and used for interventions in which entry from below the patient on the bed 20 is advantageous. This is especially useful when the interventional procedure is to be conducted below the patient in a lateral direction.

The modular intervention bed 20 can also be configured to include attaching a piece of equipment 24 to the trestle 30. Such equipment 24 can be a rod from which intravenous fluids are hung or monitoring equipment is attached.

Some intervention procedures require an operator to have access to the patient from the end of the bed such as during a stereotaxic breast biopsy for lateral, cranial-caudal or oblique interventional orientations. To accommodate such requirements, the modular intervention bed 20 can be configured in a cantilevered fashion by moving a portion 54 of the couch 50 over an edge 41 of the trestle 30. In this configuration the intervention area 32 is beyond the edge 41 of the trestle 30 but below the patient couch 50. The two mats 54 that define the opening 52 extend beyond the edge 41 of the trestle 30.

Thus, there is provided a modular intervention bed that can be reconfigured to allow access to a patient in an intervention area 32 during a medical, topographic imaging procedure. Although the invention has been described in conjunction with specific embodiments thereof, it is evident that many alternatives, modifications and variations will be apparent to those ordinarily skilled in the art. For example, the trestle components can be molded into single unitary pieces or they can be assembled with separate risers and cross-pieces. The rollers can be wheels or balls maintained in a socket or a formed curved protrusion that aligns with the guides mounted on the trestle. Accordingly, it is intended to embrace all such alternatives, modifications and variations that fall within the spirit and scope of the appended claims.

What is claimed is:

1. A modular intervention bed for use with a medical tomographic imaging system having an associated patient transport device and an imaging device, the modular intervention bed comprising:

a trestle configured to engage the patient transport device, with the trestle having an intervention area; and, a patient couch movably mounted on the trestle, with the patient couch defining an opening corresponding to the intervention area.

2. The modular intervention bed of claim 1, wherein the couch comprises:

a plurality of patient mats with each mat connected to at least one other mat;

a pair of rollers mounted on each mat in a spaced apart relationship, with each roller proximate an outside edge of each mat;

a guide mounted on the trestle with the guide mounted and aligned with the rollers on each mat; and, a linking beam with each end of the beam attached to a mat to maintain each such mat in a spaced apart relationship and defining the opening corresponding to the intervention area.

3. The modular intervention bed of claim 2, wherein the trestle comprises a first portion and a second portion, with each portion configured to engage the patient transport device with the first portion a selected distance from the second portion, wherein the distance between the two portions defines the intervention area.

4. The modular intervention bed of claim 2, including a second guide mounted on the trestle, with each guide mounted and aligned with the rollers along each outside edge of each mat.

5. The modular intervention bed of claim 2, wherein the couch is configured by one of addition and removal of a mat.

6. The modular intervention bed of claim 1, wherein the trestle includes a pair of risers maintained in a spaced apart relationship by at least one crosspiece connected to each riser.

7. The modular intervention bed of claim 6, including a clamp configured to couple each riser to the patient transport device.

8. The modular intervention bed of claim 1, wherein the trestle and couch are composed of a non-metallic material.

9. The modular intervention bed of claim 1, including a side cover attached to at least one of the trestle and couch.

10. A modular intervention bed for use with a medical tomographic imaging system having an associated patient transport device and an imaging device, the modular intervention bed comprising:

a means for supporting configured to engage the patient transport device, with the means for supporting having an intervention area; and, a means for reclining movably mounted on the means for supporting, with the means for reclining defining an opening corresponding to the intervention area.

11. The modular intervention bed of claim 10, wherein the means for reclining comprises:

a plurality of means for lying, with each means for lying connected to at least one other means for lying;

a pair of means for rolling mounted on each means for lying in a spaced apart relationship, with each means for rolling proximate an outside edge of each means for lying;

a guide mounted on the means for supporting with the guide aligned with the means for rolling on each means for lying; and, a means for linking, with each end of the means for linking attached to a means for lying to maintain each such means for lying in a spaced apart relationship and defining the opening corresponding to the intervention area.

12. The modular intervention bed of claim 11, wherein the means for supporting comprises a first portion and a second portion, with each portion configured to engage the patient transport device with the second portion a selected distance from the first portion, wherein the distance between the two portions defines the intervention area.

13. The modular intervention bed of claim 11, including a second guide mounted on the means for supporting, with each guide mounted and aligned with the means for rolling along each outside edge of each means for lying.

14. The modular intervention bed of claim 10, wherein the means for reclining is configured by one of addition and removal of a means for lying.

15. The modular intervention bed of claim 10, wherein the means for supporting includes a pair of means for raising maintained in a spaced apart relationship by at least one crosspiece connected to each means for raising.

16. The modular intervention bed of claim 15, including a means for clamping configured to couple each means for raising to the patient transport device.

17. The modular intervention bed of claim 10, wherein the means for supporting and means for reclining are composed of a nonmetallic material.

18. The modular intervention bed of claim 10, including a means for covering attached to at least one of the means for supporting and the means for reclining.

19. A method for providing access to a patient on a patient transport device for a medical imaging procedure, the method comprising the steps of:

placing a trestle on the patient transport device, with the trestle having an intervention area;

placing a movable patient couch on the trestle, with the patient couch having an opening corresponding to the intervention area;

securing the trestle to the patient transport device;

placing the patient on the patient couch;

orientating the patient on the couch to expose the patient in the intervention area; and, performing the medical imaging procedure on the patient including accessing the patient in the intervention area.

20. The method of claim 19, including the steps of:

reconfiguring the couch by adding or removing a mat;

reconfiguring the trestle to correspond to the reconfigured couch; and, aligning the reconfigured couch with the reconfigured trestle, wherein a new intervention area is provided for access to the patient.

21. The method of claim 19, including the step of attaching a piece of equipment to the trestle.

22. The method of claim 19, including the step of moving a portion of the couch over an edge of the trestle in a cantilevered fashion.

* * * * *